United States Patent [19]

Broughton

[11] 4,036,745

[45] July 19, 1977

[54] PROCESS FOR SEPARATING NORMAL AND ISOPARAFFINS

[75] Inventor: Donald B. Broughton, Evanston, Ill.

[73] Assignee: UOP Inc., Des Plaines, Ill.

[21] Appl. No.: 616,470

[22] Filed: Sept. 24, 1975

[51] Int. Cl.$^2$ .......................................... C10G 25/04
[52] U.S. Cl. ........................ 208/310 Z; 260/674 SA; 260/676 MS
[58] Field of Search ............ 208/310 Z; 260/676 MS, 260/674 SA

[56] References Cited

U.S. PATENT DOCUMENTS

| | | | |
|---|---|---|---|
| 3,205,166 | 9/1965 | Ludlow et al. | 208/310 Z |
| 3,378,486 | 4/1968 | Powers et al. | 208/310 Z |
| 3,715,409 | 2/1973 | Broughton | 208/310 Z |
| 3,753,896 | 8/1973 | Bryan et al. | 208/310 Z |

*Primary Examiner*—Herbert Levine
*Attorney, Agent, or Firm*—James R. Hoatson, Jr.; Thomas K. McBride; William H. Page, II

[57] ABSTRACT

An improved process for separating normal paraffins from a feed stream containing a mixture of normal paraffins, isoparaffins and aromatic hydrocarbons to produce a normal paraffin product stream having a reduced concentration of contaminant aromatic hydrocarbons. The general process comprises the steps of contacting the feed stream with an adsorbent comprising a crystalline aluminosilicate wherein normal paraffins are adsorbed within the pores of the adsorbent and contaminant aromatics are adsorbed on the surface of the adsorbent and subsequently contacting the adsorbent with a desorbent material to remove both adsorbed normal paraffins and contaminant aromatics. The improvement resides in using a two-stage desorption step in which a first desorbent material contacts the adsorbent and removes surface-adsorbed aromatic contaminants and then a second desorbent material contacts the adsorbent to remove normal paraffins adsorbed within the pores of the adsorbent.

14 Claims, 1 Drawing Figure

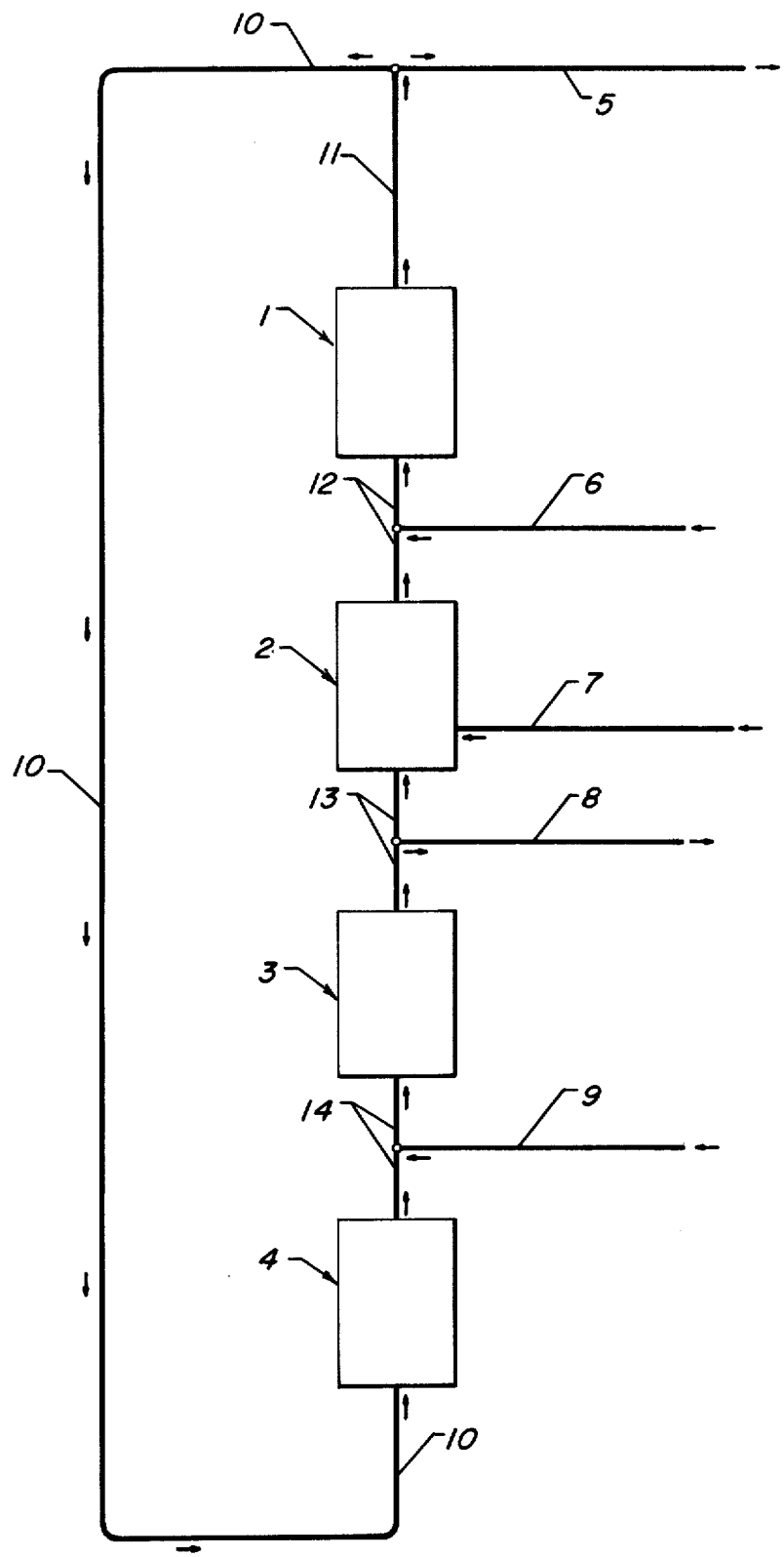

PROCESS FOR SEPARATING NORMAL AND ISOPARAFFINS

BACKGROUND OF THE INVENTION

1. Field of the Invention

The field of art to which this invention pertains is hydrocarbon separation. Specifically this invention relates to a process which utilizes a crystalline aluminosilicate to separate normal parafins from isoparaffins. More specifically this invention relates to an improved normal paraffin separation process wherein a two-step desorption step is utilized to produce a high-purity normal paraffin product stream. 2. Description of the Prior Art Applicant recognizes the abundance of prior art in the separation field especially that art relating to countercurrent fixed bed type operations which are commonly referred to as simulated countercurrent flow fixed bed type operations as particularly exemplified in my U.S. Pat. No. 2,985,589.

Specific prior art patents which are considered closely related to the present invention are Broughton and Gerhold U.S. Pat. No. 2,985,589; Broughton U.S. Pat. No. 3,274,099; Pharis et al U.S. Pat. No. 3,732,325; Neuzil U.S. Pat. No. 3,696,107; Pharis et al U.S. Pat. No. 3,723,302; Adams et al U.S. Pat. No. 3,733,261; and Broughton U.S. Pat. No. 3,715,409. All of these patents relate to simulated countercurrent solid-fluid separation processes in which an extract component of a feed stream is separated by selective adsorption on a particular adsorbent and subsequently recovered in a higher concentration than that in the feed stream as a product stream. In each process there are various zones representing quantities of adsorbent material in which individual operations are taking place. In each, at least three operational zones are utilized: an adsorption zone, a purification zone and a desorption zone. In the adsorption zone, the selectively adsorbed extract material and perhaps some contaminant materials are adsorbed while the less selectively retained raffinate materials generally remain in the interstitial void spaces surrounding the adsorbent. The basic operation taking place in the purification zone is the purification of the absorbed extract materials present in the adsorbent; the adsorbent in "passing" through the purification zone becomes more concentrated with the extract material and less concentrated with raffinate materials. In the desorption zone a desorbent material removes the absorbed extract material from the adsorbent.

The first patent discloses the basic concept of a simulated countercurrent solid-fluid contacting process employing a fixed bed of solid adsorbent having moving input and output streams which allow a segregation of zones in which separate functions are taking place in order to separate a feed stream into a raffinate product component and an extract product component.

The second U.S. Pat. No. 3,274,099 includes the same basic processing steps as the first patent but also includes an additional input stream into the purification zone, which is located between the adsorption zone and the desorption zone. The input stream is a sweeping agent, a raffinate-type (that is, a material which is relatively unadsorbed by the adsorbent) compound having a boiling point to permit separation by distillation from the feed raffinate component, which is passed into the process to push raffinate material which is trapped in the interstitial void spaces between adsorbent particles in the purification zone back into an adsorption zone to prevent feed raffinate material from passing from the adsorption zone through the purification zone and into a desorption zone thereby contaminating an extract product with feed raffinate material. In one embodiment, the process of U.S. Pat. No. 3,274,099 is used to separate normal paraffins from isoparaffins.

U.S. Pat. No. 3,732,325 disclosed a process which employs the same basic processing steps of the first patent and a particular adsorbent to separate aromatic hydrocarbons, particularly the $C_8$ aromatics. In the process described in that patent a purification stream which comprises extract material is passed into the purification zone. The extract material can be taken either from an extract from outlet from the process or from extract material which has been separated from desorbent material in an extract stream fractionator. The purification stream containing the extract material displaces from the interstitial void spaces between the adsorbent particles any raffinate materials carried into the purification zone, removes feed contaminants adsorbed by the adsorbent and reduces the quantity of desorbent which normally surrounds the adsorbent particles in the zone when no purification stream is used.

U.S. Pat. No. 3,696,107 discloses a process for separating para-xylene from a feed stream containing a mixture of $C_8$ aromatics which employs the basic processing steps described in the first patent, a particular crystalline aluminosilicate adsorbent and a two-stage desorption operation in which a first desorbent stream contacts adsorbent in the desorption zone to effect the desorption of para-xylene from the adsorbent and a second desorbent stream contacts the adsorbent in the desorption zone to effect the pushing of desorbed para-xylenes from the interstitial void spaces between the adsorbent particles. One extract stream is withdrawn from the process.

In U.S. Pat. No. 3,723,302, which discloses a process for separating olefins from paraffins employing the basic processing steps described in the first patent and a particular adsorbent, a two-step desorption operation is again used. The process uses two desorbent materials both of which enter into the desorption zone. The first desorbent material contacts the adsorbent in the desorption zone and causes contaminants to be desorbed from the adsorbent while the second desorbent material is used to desorb the product olefins from the adsorbent contained in the same desorption zone. Two extract streams are withdrawn from the process, an extract contaminant outlet stream and an extract olefin outlet stream.

U.S. Pat. No. 3,733,261 also discloses a process for separating olefins from paraffins which employs the basic processing steps of the first patent mentioned. In that process one absorbent material is admitted in two places in the desorption zone and two extract streams are removed from the process, an extract contaminant stream containing aromatic contaminants and desorbent material and an extract olefin stream containing olefins and desorbent material.

U.S. Pat. No. 3,715,409 discloses a process for the separation of aromatic hydrocarbons which employs four zones and includes the steps of: passing an extract material input stream into the purification zone to effect the desorption and displacement of raffinate material; passing at least a portion of the raffinate output stream passing out of the absorption zone into the buffer zone to effect desorption and displacement of desorbent material; and, passing a raffinate input stream into an adsorption zone to effect displacement of desorbent from the adsorbent in that zone.

The process of this invention relates to an improved process for separating normal paraffins from a feed stream containing normal paraffins, isoparaffins and aromatic hydrocarbons. The process in one embodiment employs a simulated moving bed countercurrent processing scheme in which at least three zones are shifted through the mass of adsorbent to allow various portions of the mass of adsorbent to function as absorption, purification and desorption zones. The improvement comprises using a two-step desorption operation in which (1) a first desorbent material contacts adsorbent containing adsorbed normal paraffins and aromatics in the purification zone and desorbs the aromatics; and, (2) a second desorbent material contacts the adsorbent containing the adsorbed normal paraffins in the desorption zone and desorbs the normal paraffins. The improvement permits the production of a normal paraffin product containing reduced quantities of aromatic hydrocarbon contaminants.

Prior to my invention various methods of pre-treatment of the feed stream or post-treatment of the normal paraffin product or both have been used to remove all or a portion of the aromatic contaminants. Such methods have included acid washing and hydrogenation processes. By the process of my invention the concentration of aromatic contaminants in the normal paraffin product can be reduced in the normal paraffin separation process itself thus possibly eliminating the need for such feed stream pre-treatment and product post-treatment or at least the severity of such treatments.

My invention has particular utility where the normal paraffins are to be used as raw materials for the biochemical production of proteins intended for animal or human consumption and where therefore aromatic contaminants are particularly objectionable.

SUMMARY OF THE INVENTION

It is, accordingly, a broad objective of my invention to provide an improved normal paraffin separation process in which the concentration of contaminant feed aromatics in the normal paraffin produce stream can be reduced by employing a first desorbent material to remove only the surface-adsorbed contaminant aromatics from the adsorbent prior to contacting the adsorbent with a second desorbent material to desorb the adsorbed normal paraffins. The normal paraffin product is thereafter recovered in high purity and with low concentrations of aromatic hydrocarbon contaminants.

In brief summary my invention is, in its broadest embodiment, an improved process for the separation of normal paraffins from a feed stream containing a mixture of normal paraffins and isoparaffins along with aromatic hydrocarbons which process employs an adsorbent comprising a shape-selective zeolite and comprises the steps of: (a) contacting said absorbent with said feed at adsorption conditions to effect the selective adsorption of normal paraffins and a portion of the aromatic hydrocarbons by the adsorbent; (b) removing a raffinate stream comprising less selectively adsorbed isoparaffins from said adsorbent; (c) contacting said absorbent with a desorbent material at desorption conditions to effect the desorption of normal paraffins from said adsorbent; (d) removing from said adsorbent an extract stream comprising normal paraffins; and, (e) passing at least a portion of said extract stream to a separation means and therein separating at separation conditions normal paraffins from desorbent material, the improvement which comprises using a two-step desorption operation which comprises the steps of (i) contacting at first desorption conditions said adsorbent with a first desorbent material to effect the desorption of said feed aromatic hydrocarbons; (ii) removing a first extract stream comprising said feed aromatic hydrocarbons and said first desorbent material from said adsorbent; (iii) contacting at second desorption conditions said adsorbent with a second desorbent material to effect the desorption of normal paraffins; (iv) removing a second extract stream comprising normal paraffins and second desorbent material from said adsorbent; and (v) passing at least a portion of said second contact extract stream to a separation means and therein separating at separation conditions normal paraffins from said second desorbent material.

In another embodiment my invention is an improves process for the separation of normal paraffins from a feed stream comprising a mixture of normal paraffins, isoparaffins and aromatic hydrocarbons which process employs an adsorbent comprising a shape-selective zeolite and comprises the steps of: (a) maintaining net fluid flow through a column of an adsorbent in a single direction, which column contains at least zones having separate operational functions occurring therein and being serially interconnected with the terminal zones of said column connected to provide a continuous connection of said zones; (b) maintaining an adsorption zone in said column, said zone defined by the adsorbent located between a feed input stream at an upstream boundary of said zone and a raffinate output stream at a downstream boundary of said zone; (c) maintaining a purification zone immediately upstream from said adsorption zone, said purification zone defined by the adsorbent located between an extract output stream at an upstream boundary of said purification zone and said feed input stream at a downstream boundary of said purification zone, said purification zone having a sweeping agent input stream located upstream from said feed input stream; (d) maintaining a desorption zone immediately upstream from said purification zone, said desorption zone defined by the adsorbent located between a desorbent input stream at an upstream at an upstream boundary of said zone and said extract output stream at a downstream boundary of said zone; (e) passing said feed stream into said adsorption zone at adsorption conditions to effect the selective adsorption of normal paraffins and aromatics by adsorbent in said zone and withdrawing a raffinate stream comprising isoparaffins from said zone; (f) passing a desorbent input stream into said desorption zone at desorption conditions to effect the displacement of normal paraffins from the adsorbent in said zone and withdrawing an extract output stream comprising normal paraffins and desorbent material from said zone; (g) passing at least a portion of said extract output stream to a separation means and therein separating at separation conditions normal paraffins from said desorbent material; (h) passing a sweeping agent into said purification zone; (i) periodically advancing through said column of adsorbent in a downstream direction with respect to fluid flow in said adsorption zone the feed input stream, raffinate output stream, desorbent input stream, and extract output stream to effect the shifting of zones through said adsorbent and the production of extract output and raffinate output streams, wherein the improvement comprises using a two-step desorption operation which comprises the steps of: (i) passing into said purification zone in admixture with said sweeping agent a first desorbent material and therein desorbing at first desorption conditions aromatics from the adsorbent; (ii) withdrawing from said adsorption zone a raffinate stream comprising feed isoparaffins and aromatic hydrocarbons; (iii) passing into said desorption zone a second desorbent material, and therein desorbing at second desorption conditions normal paraffins from the adsorbent; (iv) removing an extract stream comprising normal paraffins and said second desorbent material from said desorption zone; and, (v) passing at least a portion of said extract stream to a separation means and therein separating at separation conditions normal paraffins from said second desorbent material.

Other objects and embodiments of the present invention encompass details about feed mixtures, adsorbents, desorbent materials and operating conditions all of which are hereinafter disclosed in the following discussion at each of the facets of the present invention.

DESCRIPTION OF THE INVENTION

In order to gain a better understanding of the process of this invention, the following definitions of terms that are used throughout this specification are given.

The term "feed stream" indicates a stream in the process through which feed material passes to the adsorbent. A feed material comprises one or more raffinate components. An "extract component" is a compound or type of compound that is more selectively adsorbed by the adsorbent while a "raffinate component" is a compound or type of compound that is less selectively adsorbed. In this process normal paraffins from the feed stream are extract components while feed stream isoparaffins and most of the aromatics are raffinate components. A small portion of the feed aromatics are adsorbed on the surfaces of adsorbent particles, however, and thus may be considered as an extract component in the strict sense of the term. Usually the term extract component as used herein refers to a more selectively adsorbed compound or type of compound which is to be the desired product, such as normal paraffins in this process. The term "desorbent material" shall mean generally a material capable of desorbing an extract component. Specifically, the term "first desorbent material" shall means a material capable of desorbing the surface-adsorbed feed aromatics but not capable of desorbing adsorbing normal paraffins from the adsorbent while the term "second desorbent material" shall refer to a desorbent material chosen to desorb absorbed normal paraffins. The term "sweeping agent" shall mean a raffinate-type compound admitted to the process for the primary purpose of flushing raffinate components from the non-selective void volume (hereinafter defined) of the adsorbent. The term "desorbent stream" or "desorbent input stream" indicates the stream through which desorbent material passes to the absorbent. The term "raffinate stream" or "raffinate output stream" means a stream through which most of the raffinate components are removed from the absorbent. The composition of the raffinate stream can vary from essentially 100% desorbent material to essentially 100% raffinate components. The term "extract stream" or "extract output stream" shall means a stream through which an extract material which has been desorbed by a desorbent material is removed from the absorbent.

Although it is possible by the process of this invention to produce high purity (99+%) normal paraffins at high recoveries (90% or higher), it will be appreciated that an extract component is never completely adsorbed by the absorbent, nor is a raffinate component completely non-adsorbed by the adsorbent. Therefore, small amounts of a raffinate component can appear in the extract stream and, likewise, small amounts of an extract component can appear in the raffinate stream. The extract and raffinate streams then are further distinguished from each other and from the feed mixture by the ratio of the concentrations of an extract component and a raffinate component appearing in the particular stream. More specifically, the ratio of the concentration of more selectively adsorbed normal paraffins to that of the less selectively adsorbed isoparaffins will be lowest in the raffinate stream, next highest in the feed mixture, and the highest in the extract stream. Likewise, the ratio of the concentration of the less selectively adsorbed isoparaffins to that of the more selectively adsorbed normal paraffins will be highest in the raffinate stream, next highest in the feed mixture, and the lowest in the extract stream. In one embodiment of my process there will be two extract streams, one containing desorbed feed aromatics, first desorbent material and essentially no normal paraffins and one containing normal paraffins, second desorbent material and a reduced concentration of feed aromatics. In another embodiment of my process there will be one extract stream which will contain normal paraffins, second desorbent material and a reduced concentration of feed aromatics. Almost all of the feed aromatics, along with feed isoparaffins and first desorbent material, will appear in the raffinate stream in this latter embodiment. The composition of the extract stream, particularly in this latter embodiment, can vary from essentially 100% desorbent material to essentially 100% extract components.

The term "selective pore volume" of the adsorbent is defined as the volume of the adsorbent which selectively adsorbs extract components from the feed stock. The term "non-selective void volume" of the adsorbent is the volume of the adsorbent which does not selectively retain extract components from the feed stock. This volume includes the cavities of the absorbent which contain no adsorptive sites and the interstitial void spaces between adsorbent particles. The selective pore volume and the non-selective void volume are generally expressed in volumetric quantities and are of importance in determining the proper flow rates of fluid required to be passed into an operational zone for efficient operations to take place for a given quantity of adsorbent.

When adsorbent "passes" into an operational zone (hereinafter defined and described) its non-selective void volume together with its selective pore volume carries fluid into that zone. The non-selective void volume is utilized in determining the amount of fluid which should pass into the same zone in a countercurrent direction to the absorbent to displace the fluid present in the non-selective void volume. If the fluid flow rate passing into a zone is smaller that the non-selective void volume rate of adsorbent material passing into that zone, there is a net entrainment of liquid into the zone by the adsorbent. Since this net entrainment is a fluid present in non-selective void volume of the adsorbent, it in most instances comprises less selectively retained feed components.

The selective pore volume of an adsorbent can in certain instances adsorb portions of raffinate material from the fluid surrounding the adsorbent since in certain instances there is competition between extract material and raffinate mateial for adsorptive sites within the selective pore volume. If a large quantity of raffinate material with respect to extract material surround the adsorbent, raffinate material can be competitive enough to be adsorbed by the adsorbent.

Feed stocks which can be used in the process of this invention will be hydrocarbon fractions having a carbon number range of from about 6 carbon atoms per molecule up to about 30 carbon atoms per molecule. Typically, the carbon number range of the hydrocarbon fractions will be rather narrow, such as from about three to about six carbon numbers. A $C_{10}$ to $C_{15}$ kerosine fraction is a typical feed stream. Feed streams will contain normal paraffins, isoparaffins and aromatics in varying concentrations but little or no olefins. Depending on the type of crude from which the hydrocarbon fraction is derived and the carbon number range of the fraction, the normal paraffin concentration will typically range from about 20 to about 60 vol. % of the feed and the aromatic concentration from about 10 to about 30 vol. % of the feed. There may be more unusual feed streams which have aromatic concentrations of only about 2 to about 4 vol. % of the feed stream. Since the feed aromatics, like the isoparaffins, cannot enter the pores of adsorbent used in this process because their cross-sectional diameter is too great, almost all of the aromatics appear in the raffinate stream. A small portion, however, is rather tenaciously adsorbed on the surfaces of the adsorbent particles and ultimately appears as a contaminant in the extract (normal paraffin) product. The feed aromatics can include monocyclic aromatics such as benzene or alkylbenzenes; indanes or alkyl-indanes; and bicyclic aromatics including naphthalenes, biphenyls, or the acenaphthenes. The abovementioned aromatic contaminants can be generally characterized as having the general formula of $C_nH_{2n-J}$, where J as used in the mass spectrometer art, indicates a specific number which when supplied in the abovementioned empirical formula can allow distinctive characterization of complicated aromatic types. We have found that certain $J_6$ and $J_{12}$ aromatic hydrocarbons are those which are most strongly held on the adsorbent. Other types of aromatic hydrocarbons such as the $J_8$ or $J_{10}$ or even $J_{16}$ type hydrocarbons would also be strongly adsorbed.

The sweeping agent, previously defined, will preferably have a boiling point which differs sufficiently from the boiling point of the feed stream raffinate component to be readily separated from the raffinate stream by accessory, subsequent distillation. Thus in this process the sweeping agent may be selected from the higher or lower boiling homologs of the branched chain or cyclic components of the feed stock. As a specific instance, a suitable sweeping agent which may be used in the separation of normal paraffins from a $C_{10}$ to $C_{15}$ feed stock is isooctane which is not adsorbed by the adsorbent and which is separable from the $C_{10}$–$C_{15}$ raffinate components by distillation.

The sweeping agent is supplied at a rate sufficient to substantially equal the volume of void space between the particles of adsorbent passing a given point in the process cycle at a given rate of circulation, thereby substantially and continuously removing the entrained material, primarily raffinate components, from between the particles of adsorbent as the latter is circulated through the process flow. The displaced raffinate components join the fluid stream flowing in a downstream direction of flow and are eventually removed from the circulating fluid phase by withdrawal as the raffinate output stream which may then be passed to a raffinate stream separation means where raffinate components can be recovered. The preferred rate of charging the sweeping agent in the purification zone is at a rate of flow equal to or greater than the rate of flow of the void spaces between the particles of adsorbent a rate which is dependent in any particular instance upon the particle size of the adsorbent, whether a moving bed or fixed be process is used, and other factors.

The desorbent materials used in the process of this invention should be materials that are easily separated from the feed mixture. Both the raffinate stream and the extract stream (or streams, in those embodiments where there is more than one extract stream) are removed from the adsorbent in admixture with desorbent materials. Without a method of separating these desorbent materials the purity of the extract components and the raffinate components if their recovery is desired would not be very high nor would the desorbed materials be available for reuse in the process. It is contemplated therefore that the desorbent materials will have a different boiling range than the feed mixture fed to the adsorbent which would allow fractionation to be used to separate the raffinate and extract components and allow recovery of the desorbent materials for possible reuse in the process.

First desorbent materials to be used in this process will comprise aromatic hydrocarbons which have a different boiling point than the feed mixture. In the embodiment of my process where a sweeping agent is employed, the first desorbent material will also preferably have a boiling point different from the sweeping agent to permit separation therefrom by distillation. First desorbent materials which can be used in this process can comprise such aromatics as benzene, toluene, the xylene isomers, and ethylbenzene. In the example previously given where normal paraffins were to be separated from a $C_{10}$–$C_{15}$ feed stream and isooctane was used as the sweeping agent, para-xylene or ethylbenzene would be examples of suitable first desorbent materials, Where the first desorbent mixture is used in admixture with the sweeping agent, the concentration of the first desorbent material in the mixture can range from about 5 to near 100 vol. % of the total mixture. More preferably the concentration will be in the range of from about 15 to about 40 vol. %. Since the fraction of the first desorbent material is to desorb only the surface-adsorbed feed aromatics, it is also important that the first desorbent material contain little or no second desorbent material to avoid desorbing the normal paraffins. Preferably the concentration of second desorbent material in the first desorbent material will be less than about 1.0 vol.%.

The second desorbent material can comprise any normal paraffin having a boiling point different than that of the feed mixture. A second desorbent comprising normal pentane is frequently used since it is easily separable from feed stocks generally used in this process. The second desorbent material can be 100% normal paraffins or can be lesser concentrations of normal paraffins in admixture with an isoparaffin diluent. When used in admixture with a diluent the concentration of normal paraffins will typically be from about 40 to about 80 vol. % of the mixture. It is important that the second desorbent material contain little or no first desorbent material since the presence of aromatics hinders the desorption of normal paraffins by the second desorbent material. Preferably the concentration of first desorbent material in second desorbent material will be less than about 0.1 vol. %.

Solid adsorbents contemplated for use herein shall comprise shape-selective zeolites commonly referred to as molecular sieves. The term "shape-selective" refers to the zeolite's ability to separate molecules according to shape or size because of zeolite's pores of fixed cross-sectional diameter. The zeolites belong to a group of aluminum silicate crystals having a framework structure in which every tetrahedron of $SiO_4$ or $AlO_4$ shares all its corners with other tetrahedra, thus accounting for all the silicon, aluminum and oxygen atoms in the structure. These crystals have a chemical formula in which the ratio $(Si+Al):(O)$ is 1 to 2. Of the several types of known zeolites, only those having rigid frameworks are suitable molecular sives. When originally formed, the zeolite crystals contain water in the interstices defined by the framework. On moderate heating this water can be driven off and the open interstices are then of uniform size and can admit compounds whose maximum critical molecular diameters are not substanially greater than the minimum diameters of the interstices. The pure zeolite molecular sieves, particularly the synthetic ones, generally are produced in the form of soft, powdery masses of small crystals. For use in commercial processes these zeolite crystals may be composited with binder materials such as clays, alumina or other materials, to form stronger, more attrition-resistant particles.

Adsorbents contemplated for use in this process will comprise zeolites having uniform pore diameters of 5 Angstroms such as chabazite or particularly such as Linde's commercially-available type 5A molecular sieve. As obtained commercially this latter material is usually in the form of an extrudate or a pellet or in granular form and contains pure 5A zeolite and a binder material such as clay. The adsorbent utilized in this process will generally be in the form of particles having a particle size range of from about 20 to about 40 mesh size.

The adsorbent may be employed in the form of a dense compact fixed bed which is alternatively contacted with the feed mixture and desorbent materials. In the simplest embodiment of the invention the adsorbent is employed in the form of a single static bed in which case the process is only semi-continuous. In another embodiment a set of two or more static beds may be employed in fixed-bed contacting with appropriate valving so that the feed mixture is passed through one or more adsorbent beds while the desorbent materials can be passed through one or more of the other beds in the set. The flow of feed mixture and desorbent materials may be either up or down through the desorbent. Any of the conventional apparatus employed in static bed fluid-solid contacting may be used.

Countercurrent moving-bed or simulated moving-bed countercurrent flow systems, however, have a much greater separation efficiency than fixed adsorbent bed systems and are therefore preferred. In the moving-bed or simulated moving-bed processes the adsorption and desorption operations are continuously taking place which allows both continuous production of an extract and a raffinate stream and the continual use of feed and desorbent streams. One preferred embodiment of this process utilizes what is known in the art as the simulated moving-bed countercurrent flow system. The operating principles and sequence of such a flow system are described in my U.S. Pat. No. 2,985,589. In such a system it is the progressive movement of multiple liquid access points down an adsorbent chamber that simulates the upward movement of adsorbent contained in the chamber. Only four of the access lines are active at any one time; the feed input stream, desorbent inlet stream, raffinate outlet stream, and extract outlet stream access lines. Coincident with this simulated upward movement of the solid adsorbent is the movement of the liquid occupying the void volume of the packed bed of adsorbent. So that countercurrent contact is maintained, a liquid flow down the adsorbent chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divided the adsorbent chamber into separate zones, each of which has a different function. In this embodiment of my process it is generally necessary that three separate operational zones be present in order for the process to take place although in some instances an optional fourth zone may be used.

The adsorption zone, zone 1, is defined as the adsorbent located between the feed inlet stream and the raffinate outlet stream. In this zone, the feed stock contacts the adsorbent, an extract component is adsorbed, and a raffinate stream is withdrawn. Since the general flow through zone 1 is from the feed stream which passes into the zone to the raffinate stream which passes out of the zone, the flow in this zone is considered to be a downstream direction when proceeding from the feed inlet to the raffinate outlet streams.

Immediately upstream with respect to fluid flow in zone 1 is the purification zone, zone 2. The purification zone is defined as the adsorbent between the extract outlet stream and the feed inlet stream. The basic operations taking place in zone 2 are the displacement from the non-selective void volume of the adsorbent of any raffinate material carried into zone 2 by the shifting of adsorbent into this zone and the desorption of any raffinate material adsorbed within the selective pore volume of the adsorbent or adsorbed on the surfaces of the adsorbent particles. Purification is effected by the use of a sweeping agent and a first desorbent material along with, in some instances, a portion of extract stream material which can comprise both extract material and second desorbent material passing out of zone 3 into zone 2 at at zone 2's upstream boundary the extract outlet steam. The flow of material in zone 2 is in a downstream direction from the extract outlet stream to the feed inlet stream.

Immediately upstream of zone 2 with respect to the fluid flowing in zone 2 is the desorption zone or zone 3. The desorption zone is defined as the adsorbent between the desorbent inlet and the extract outlet stream. The function of the desorption zone is to allow a second desorbent material which passes into this zone to displace the normal paraffins which were adsorbed upon the adsorbent during a previous contact with feed in zone 1 in a prior cycle of operation. The flow of fluid in zone 3 is essentially in the same direction as that of zones 1 and 2.

In some instances an optional buffer zone, zone 4, may be utilized. This zone, defined as the adsorbent between the raffinate outlet stream and the desorbent inlet stream, if used, is located immediately upstream with respect to the fluid flow to zone 3. Zone 4 would be utilized to conserve the amount of desorbent utilized in the desorption step since a portion of the raffinate stream which is removed from zone 1 can be passed into zone 4 to displace desorbent material present in that zone out of that zone into the desorption zone. Zone 4 will contain enough adsorbent so that raffinate material present in the raffinate stream passing out of zone 1 and into zone 4 can be prevented from passing into zone 3 thereby contaminating extract stream removed from zone 3. In the instances in which the fourth operational zone is not utilized the raffinate stream passed from zone 1 to zone 4 must be carefully monitored in order that the flow directly from zone 1 to zone 3 can be stopped when there is an appreciable quantity of raffinate material present in the raffinate stream passing from zone 1 into zone 3 so that the extract outlet stream is not contaminated. For additional description of zone operation see the Description of the Drawing section of this specification.

Both liquor and vapor phase operations can be used in the process of this invention; however, the liquid phase operations are preferred because of the lower temperature requirements and slightly improved selectivities associated with the lower temperatures employed in liquid phase operations. Adsorption conditions will include a temperature range of from 40° C. to about 250° C. and a pressure range of from about atmospheric to about 500 psig. First and second desorption conditions will include the same range of temperatures and pressures as used for adsorption conditions.

DESCRIPTION OF THE DRAWING

The attached drawing illustrates one embodiment of the process of this invention. Briefly the drawing shows four separate operating zones, adsorption zone 1, purification zone 2, desorption zone 3 and optional buffer zone 4; connecting conduits 10, 11, 12, 13 and 14; input streams 6, 7, and 9 and output streams 5 and 8. The four zones as shown in the drawing are stationary beds of solid adsorbent particles but may in other instances consist of a series of one or more individual chambers connected in a serial manner. Each of the individual zones may be a single chamber or a series of beds stacked upon one another in a column making up a zone. Thus in some instances each of the above zones would contain the same general quantity of adsorbent and have the same general physical dimensions, but in other instances some zones may require more adsorbent than other zones.

As the drawing shows, the overall net liquid flow is in an upward direction but in some instances a zone may be operating in a manner to allow flow of fluid for a certain period of time in a direction opposite to the overall net flow of fluid. The adsorbent particle flow can be considered to be in a downward direction to help in understanding the processing steps taking place in various zones. During normal fixed-bed countercurrent operations the adsorbent material remains stationary and the individual adsorption, purification, desorption and buffer zones, as defined, are moved through the adsorbent by shifting various input and output streams in a unidirectional manner to allow fluid to flow in a countercurrent direction with respect to solid adsorbent and to continuously produce extract and raffinate streams. In most instances the shifting of the input and output streams along the fixed bed of adsorbent is done simultaneously and in the same direction along the bed of adsorbent. In other instances it is desired that two or more zonal functions take place in the adsorbent between two input and output streams before the input and output streams are shifted.

In accordance with the definition of the zones previously given, the adsorption zone 1 is the adsorbent material located between feed input stream 6 and raffinate stream output stream 5 which is connected to zone 1 via line 11. Purification zone 2 is located immediately upstream from adsorption zone 1 and shares the feed input stream 6 as a common boundary with adsorption zone 1. Purification zone 2 is the adsorbent located between the extract outlet stream 8 and feed input stream 6. Immediately upstream from the purification zone 2 is desorption zone 3 which shares the extract outlet stream 8 as a common boundary with purification zone 2. Desorption zone 3 is the adsorbent between extract outlet stream 8 and desorbent inlet stream 9. Immediately upstream from desorption zone 3 is optional buffer zone 4 which shares the desorbent inlet stream 9 as a common boundary with desorption zone 3 and shares raffinate outlet stream 5 as a common boundary with purification zone 2. Optional zone 4 is the adsorbent located between desorbent inlet stream 9 and raffinate output stream 5. In some instances an optional fourth zone is used to prevent contamination of the extract material with raffinate material from zone 1.

Terminal zones 1 and 4 are connected by connecting conduits 10 and 11. The connecting conduits allow a portion of the fluid flowing out of zone 1 via line 11 to eventually flow via line 10 into zone 4 or zone 3 depending whether or not the optional zone is utilized, thereby allowing a closed-loop circulation of fluid. Lines 12, 13 and 14 are other connecting conduits connecting, respectively, zones 1 and 2, zones 2 and 3 and zones 3 and 4 to allow a continuous passage of fluid from one zone to and through all the other zones. Specifically, the material passing out of the adsorption zone 1 via line 11 can pass into line 5 or a portion of it may be diverted via line 10 to be passed eventually into buffer zone 4. Feed stock which passes into the process via line 6 passes through connecting conduit 12 and into the adsorption zone 1. In some instances a portion of the fluid material which passes out of purification zone 2 via line 12 may pass in admixture with feed material, entering the process via line 6, into adsorption zone 1. Line 13 is a connecting conduit which allows, in some instances, a portion of the fluid material withdrawn from desorption zone 3 via line 13 to bypass line 8 and pass via line 13 into purification zone 2. In a similar manner line 14 connects buffer zone 4 and desorption zone 3 and a portion of the fluid material leaving buffer zone 4 is allowed to pass out of that zone, to contact material passing into the process via desorbent input stream line 9 and to pass in admixture with desorbent through line 14 into the desorption zone 3. This allows a reduction in process desorbent requirements from external sources — namely, desorbent input stream line 9. Line 10 can contain a pump or other fluid displacement means in order to induce flow in the process in a direction passing from line 11 through line 10 and into buffer zone 4.

Other pumps and valves located on the input and output lines and the lines which connect the various zones which control flow into, out of and through the process are not shown. It is presumed they could be located where necessary by one skilled in the art to induce and control proper fluid flow in the process. The input streams passing into the various zones can be connected to high pressure sources or pumping means in order to induce flow into the process and the streams which pass out of the process can be regulated by back pressure valves in order to maintain regulated pressure drops through the zones to induce fluid flow. In some instances unidirectional flow directing devices such as check valves can be located on the conduits between the various zones where a pump around circuit is not utilized.

The operations taking place in various zones shown in the drawing are as follows:

Essential operations taking place in zone 1 are the contacting of an adsorbent material with a feed stream and the selective adsorption of an extract component within the selective pore volume of the adsorbent and the adsorption of a small quantity of a raffinate component on the surfaces of the adsorbent particles. In this separation process the extract component is normal paraffins and the raffinate component that clings to the surface of adsorbent is aromatic hydrocarbons. In the prior art processes these surfaced-adsorbed aromatics ultimately appear as contaminants in the extract stream. A feed stream passes into the process via line 6, and since the overall general direction of fluid flow within that zone is in upward direction, passes through line 12 along with any material which may pass out of zone 2 via line 12 into zone 1.

As feed is passed into zone 1 an equal volume of raffinate stream material is displaced from zone 1 leaving that zone via line 11. A portion or all of the raffinate stream which passes through line 11 may be removed from the process via line 5 with any portion not removed passing through line 10 into either zone 3 or zone 4 depending upon whether or not optional zone 4 is used in the process. Raffinate output stream line 5 may be directed to a separation means (not shown) for separation of raffinate components from desorbent materials.

The adsorbent in zone 1 may be envisioned as moving in a direction countercurrent to the fluid flow in the zone. A simulated flow of solids occurs into and out of the adsorption zone when the zones are shifted during a portion of the entire cycle of operations. The adsorbent entering zone 1 comes from zone 3 or zone 4 depending upon whether or not optional zone 4 is used in the process. If optional zone 4 is not employed then the adsorbent leaving zone 3 and entering zone 1 will generally contain desorbent material in both the non-selective void volumes and the selective void volumes. In instances where zone 4 is employed then a portion of the raffinate stream can be passed via line 10 into zone 4 to displace desorbent material from the non-selective void volumes present in the adsorbent particles in zone 4 into zone 3 via line 14. The adsorbent which then passes from the buffer zone 4 into the adsorption zone 1 contains for the most part desorbent material located within the adsorbent particle's selective pore volume which the extract material is required to desorb in zone 1. Although not shown in the drawing, it is possible to have desorbent material essentially removed from the selective pore volumes by additionally contacting the adsorbent with relatively high purity raffinate material prior to the contacting of the adsorbent with the feed input stream at the upstream portion of the adsorption zone. This feature which is part of a process described in my U.S. Pat. No. 3,715,409, is desirable in many systems because it has been found that the absence of desorbent in the adsorption zone enhances the ability of the adsorbent to selectively adsorb and retain the extract component relative to the raffinate component.

The adsorbent, in passing through the adsorption zone 1 from its downstream boundary towards its upstream boundary with respect to fluid flow in that zone, adsorbs extract material from the feed input stream. As the adsorbent passes out of the adsorption zone it contains extract material and some raffinate material located within the selective pore volume of the adsorbent and some raffinate material adsorbed on the adsorbent particle surfaces. The material present in the nonselective void volume of adsorbent is generally raffinate material with small portions of extract material from the feed stock which have not been adsorbed by the adsorbent. This adsorbent then passes into the purification zone 2 passing into that zone at its downstream boundary feed input stream line 6.

When the adsorbent passes into the purification zone 2 from the adsorption zone 1, it generally contains some raffinate material present in the adsorbent's selective pore volume, in the non-selective void volume, and adsorbed on the surfaces of the adsorbent particles. The function of purification zone 2 then is to eliminate raffinate material from both the adsorbent's selective pore volume, the adsorbent's non-selective void volume and the adsorbent particle surfaces so that the adsorbent leaving the purification zone via its upstream boundary (line 8) contains as little raffinate material as possible which could contaminate the extract product stream. These functions are achieved in zone 2 in different ways. First, a portion of the extract stream, a mixture of desorbent and extract material, passes into purification zone 2 from zone 3 via line 13 and displaces any raffinate material from the adsorbent's selective pore volume and sweeps displaced raffinate material and raffinate material from the adsorbent's non-selective pore volume upwardly in the rising fluid stream toward the raffinate outlet stream line 5. As shown in the drawing the purification zone also has passing into it line 7 through which flows a mixture comprising a raffinate-type sweeping agent and a first desorbent material. The sweeping agent itself supplements the washing action of the portion of the extract stream flowing into zone 2 from zone 3 via line 13. The sweeping agent also may permit removal of the feed raffinate material from the adsorbent while reducing the quantity of extract stream flowing into zone 2. A reduction in desorbent material, contained as part of the extract stream entering zone 2, enhances the adsorbent's ability to adsorb the last traces of extract material from the fluid surrounding the adsorbent in the purification zone. Additionally the sweeping agent, being a relatively non-adsorbed raffinate type material does not increase the load on the adsorbent in zone 1 of the process cycle and therefore does not reduce the capacity of the adsorbent for fresh extract entering zone 1 via line 6 as is the case with the flow of extract stream from zone 3 into zone 2 via line 13. Reasonable flow rates of the sweeping agent or the extract stream, however, do not significantly remove the relatively small amount of raffinate material that is rather tenaciously adsorbed on the surface of the adsorbent particles. While the bulk of the aromatic hydrocarbons entering the process with the feed stream pass out of the process as part of the raffinate output stream via line 5, a small portion of these aromatics are adsorbed on the adsorbent particles in zone 1, pass with the adsorbent through zone 2 and are desorbed by desorbent material in zone 3 and appear as a contaminant in the extract stream which leaves the process via line 8. For this reason, in the embodiment of my invention illustrated by the drawing, a first desorbent material in admixture with the sweeping agent enters zone 2 via line 7. By contacting the adsorbent in zone 2 with the first desorbent material the surface-adsorbed aromatic contaminants are desorbed from the adsorbent particles and pass, with the aid of the sweeping agent and the portion of the extract stream entering zone 2 via line 13, downstream through zone 2 toward the raffinate outlet stream line 5. The first desorbent material is chosen to be specific for contaminant aromatic desorption only and not the desorption of the normal paraffin extract material. Thus the adsorbent which passes out of zone 2 into zone 3 contains normal paraffins in the selective pore volume and a much-reduced concentration of contaminant aromatics on the surfaces of the absorbent particles. Although line 7 may be placed anywhere along the adsorbent material located in zone 2 from its most upstream location at extract output stream line 8 to its most downstream location at feed input stream line 6, it is preferred that line 7 be located more closely contiguous to the extract output stream line 8 so that the sweeping agent and the first desorbent material can flow through most of the length of the zone and perform their respective functions. It is possible to regulate the fluid flow through zone 2 by controlling the quantity of material passing into this zone via line 7, the material passing into this zone from zone 3 via line 13, and the amount of material passing out of the uppermost portion of the zone 2 via line 12.

The adsorbent which passes out of purification zone 2 passes into desorption zone 3 via that zone's downstream boundary, extract output stream line 8. The operation taking place in the desorption zone is essentially the removal of normal paraffins from the adsorbent. The removal is effected by contacting the adsorbent, which is now substantially free of surface-adsorbed contaminant aromatics, with a second desorbent material capable of displacing normal paraffins from the selective pore volume of the adsorbent. The desorbent input stream, comprising the second desorbent material, passes into desorption zone 3's upstream boundary via lines 9 and 14. At least a portion of the desorbed normal paraffins pass out of desorption zone 3 in admixture with second desorbent material via extract output stream line 8. Extract output stream line 8 will then pass to a separation means (not shown) where normal paraffins will be separated from desorbent material. The adsorbent leaving desorption zone 3 contains desorbent material located at both the adsorbent's selective pore volume and non-selective void volume. The adsorbent then passes into optional buffer zone 4 entering zone 4 at its downstream boundary the desorbent material input stream line 9.

Optional zone 4 in this process can be used to both conserve the amount of desorbent used in the process and prevent the contamination of extract material by raffinate material components. When operational zone 4 is used, it is possible that a portion of the raffinate stream which does not pass out of line 5 can be passed into zone 4 via lines 10 and 11 to displace desorbent material from the non-selective void volume of the adsorbent particles in zone 4 while simultaneously pushing desorbent material out of optional zone 4 via line 14 into zone 3. Since the desorbent material passes into the process via line 9 is connected to conduit 14 which connects optional zone 4 with desorption zone 3, the desorbent material which is displaced from the adsorbent in optional zone 4 tends to reduce the requirements of desorbent material which has to pass through line 9 into the process. The solid adsorbent leaving zone 4 at its upstream boundary the raffinate output stream line 5 contains essentially desorbent material in its selective pore volume with raffinate material present in the adsorbent's non-selective void volume.

In instances in which optional zone 4 is not utilized it is possible to pass some of the raffinate stream from zone 1 directly into zone 3. In such instances it is required that the composition of the material which leaves zone 1 via line 11 and which bypasses line 5 contains essentially no raffinate material. The initial raffinate material withdrawn from zone 1 contains a very high concentration of desorbent material and can be passed from lines 10 and 11 into zone 3. The flow of raffinate output stream leaving the process via line 5 may be stopped during this time. When the stream passing through lines 10 and 11 into zone 3 contains an appreciable quantity of raffinate material the flow into zone 3 via line 10 is stopped and the raffinate output stream is then withdrawn via line 5. While the raffinate materials are being withdrawn through line 5, an outside source of desorbent material can be passed into zone 3 via lines 9 or 10.

The input and output lines 5, 6, 7, 8 and 9 during normal operations carry the respective streams as described previously. In order to allow a continuous operation, it is necessary that the individual input and output streams each be shifted in the same direction and in most instances at the same time. By shifting the input and output streams throughout the bed of adsorbent, together with requiring that the terminal zones (adsorption zone 1 and buffer zone 4) have a connecting conduit, it is possible to continuously effect the individual operations taking place in the various zones. When the zones described above are being shifted by incremental amounts through stationary adsorbent material the adsorbent contacts in the following order, the adsorption zone, the purification zone, the desorption zone and the buffer zone respectively. Reference can be made to D. B. Broughton U.S. Pat. No. 2,985,589, and a paper entitled "Continuous Adsorptive Processing — A New Separation Technique" by D. B. Broughton presented at the 34th Annual Meeting of the Society of Chemical Engineers at Tokyo, Japan on Apr. 2, 1969, for further explanation of the simulated moving bed countercurrent process flow scheme.

A cyclic advancement of the input and output streams through the fixed bed of adsorbent can be accomplished by utilizing a manifold system in which the valves in the manifold are operated in a sequential manner to effect the shifting of the input and output streams in the same direction as the overall fluid flow throughout the adsorbent bed, to allow a flow of fluid with respect to solid adsorbent in a countercurrent manner. Another mode of operation which can effect the countercurrent flow of solid adsorbent with respect to fluid involves the use of a rotating disc valve in which the input and output streams are connected to the valve and the lines through which feed, extract, desorbent, purification and raffinate streams pass are advanced in the same direction through the adsorbent bed. Both the manifold arrangement and disc valve are known in the art. Specifically rotary disc valves which can be utilized in this operation can be found in U.S. Pat. Nos. 3,040,777 and 3,422,848. Both of the aforementioned patents disclose a rotary type connection valve in which the suitable advancement of the various input and output streams from fixed sources can be achieved without difficulty.

In many instances, one operational zone will contain a much larger quantity of adsorbent than some other operational zone. For instance, in some operations the buffer zone can contain a minor amount of adsorbent as compared to the adsorbent required for the adsorption and purification zones. It can also be seen that in instances in which desorbent is used which can easily desorb extract material from the adsorbent that a relatively small amount of adsorbent will be needed in a desorption zone as compared to the adsorbent needed in the buffer zone or adsorption zone or purification zone or all of them. Since it is not required that the adsorbent be located in a single column, the use of multiple chambers or a series of columns is within the scope of the invention.

It is not necessary that all of the input or output streams be simultaneously used, and in fact, in many instances some of the streams can be shut off while others effect an input or output of material. The apparatus which can be utilized to effect the process of this invention can also contain many series of individual beds being connected in a serial manner by connecting conduits and having placed upon those connecting conduits input or output taps to which the various input or output streams described herein can be attached and alternately and periodically shifted throughout the process to effect continuous operation. In some instances, the connecting conduits can be connected to transfer taps which during the normal operations do not function as a conduit through which material passes into or out of the process.

It is contemplated that the extract output stream and the raffinate output stream can pass into different separation means so that extract components and raffinate components can be separated from desorbent materials present in the above output streams. Separating means which can be used to separate the extract output stream and raffinate output stream will preferably be fractionating columns but can also include solvent extraction means or adsorptive-separation means.

The size of the units which can utilize the process of this invention can vary anywhere from those of pilot-plant scale (see for example my assignee's U.S. Pat. No. 3,706,812) to those of commercial design and can range in flow rates from as little as a few cc. an hour up to many thousands of gallons per hour.

EXAMPLE

The following example is presented to illustrate the process of the present invention and is not intended to unduly restrict the scope and spirit of the claims attached hereto. Specifically, the example illustrates the reduced concentration of aromatic contaminants in the normal paraffin extract product made possible by my process and does not purport to determine optimums for operating conditions such as temperature, pressure or types of desorbent materials used.

In this example a simulated moving bed countercurrent process for separating normal paraffins was operated with and without the use of a first desorbent material in various concentrations in admixture with the sweeping agent to determine the effect upon the concentration of contaminant aromatics in the normal paraffin product.

The apparatus used in these experiments consisted of a column containing 24 individual beds of adsorbent which were serially connected by flow conduits. The beds contained transfer taps to which were attached transfer lines which allowed material to either pass into the process or out of the process in accordance with a predetermined cycle of operations.

The apparatus used contained four separate operating zones although the process can be operated utilizing three distinct operating zones. It was not desired to utilize a three zone system since that would have required modification to the available apparatus.

Referring to the attached drawing for ease of explanation, a description of the apparatus employed in this example is as follows. Proceeding in a downstream direction from the raffinate outlet stream, line 5, into zone 4 there were four beds in zone 4. The raffinate output stream and the desorbent inlet stream, which is the downstream boundary of zone 4, were the only input and output streams in the zone. Proceeding from this stream in a downstream direction to zone 3, there were six adsorbent beds in zone 3 with no other input or output streams into the zone except for the desorbent inlet stream and the extract outlet stream, which defined the downstream boundary of zone 3. Proceeding in a downstream direction from line 8 there were a total of 8 adsorbent beds in purification zone 2. One adsorbent bed downstream from the extract stream, line 8, was line 7 through which sweeping agent in admixture with the first desorbent material entered the process. Downstream from line 7 there were six adsorbent beds with a line flush stream inlet (not shown in the drawing) passing into zone 2 in the downstream boundary of the sixth bed. The remaining bed in zone 2 was located downstream from the line flush inlet stream and immediately upstream from the downstream boundary of zone 2 which is the feed input stream, line 6. The purpose of the line flush stream was to remove feed components from the line through which feed had passed after the feed stream had been shifted to its new location in a downstream direction. This prevented the extract stream from being contaminated with raffinate during subsequent purification operations when this line carried purification material. Continuing in a downstream direction from line 6 there were six adsorbent beds in adsorption zone 1. Fresh feed input stream line 6 and raffinate output stream line 5 were the only input and output streams to this zone.

Zones 1 and 4 were at opposite ends of the 24 adsorbent bed apparatus and were connected by a conduit 10 which contained a pump to induce flow of material through this line in the same direction as the feed flow in zone 1. Conduit 10 and the pump comprise a pump-around circuit which in these experiments was necessary in order to induce overall fluid flow in the process. It is not required that a pump-around circuit be utilized to induce overall fluid flow in the process. By metering proper pressure drop across the various input and output streams connected to the adsorbent beds and placing flow directing devices such as check valves in the conduits connecting the individual adsorbent beds, the same type fluid flow would be induced.

In order for continuous simulated moving bed operation to take place, it is necessary that after a period of flow within the process that all the input and output streams be transferred at least one adsorbent bed along a downstream direction at about the same time. The shifting of the input and output streams one or more beds in a downstream direction comprises a single period of the entire cycle of operations. The entire cycle of operations takes place when enough individual period of operations had taken place to place the input and output streams in the identical position that they were in when the cycle of operations was begun. In all the experiments conducted in this example the total cycle of operations through the 24 adsorbent beds and back to the original position of the input and output streams was about 1.1 hours which amounted to about 2.75 minutes of flow for each individual period of operations of the 24 total periods of operations making up the entire cycle of operations.

The entire apparatus contained approximately 11.3 gallons of Linde 5A molecular sieves which was the adsorbent. The sieves contained approximately 1.13 gallons of selective pore volume and approximately 6.73 gallons of non-selective void volume and had a particle size distribution of approximately 16 to 40 mesh.

The feed stock was a $C_{10}$ to $C_{16}$ hydrocarbon fraction. The composition is shown in Table 1.

Table No. 1

| Feed Stock Composition | |
|---|---|
| Wt. % | |
| $n\text{-}C_{10}$ | 2.8 |
| $n\text{-}C_{11}$ | 9.2 |
| $n\text{-}C_{12}$ | 10.3 |
| $n\text{-}C_{13}$ | 10.7 |
| $n\text{-}C_{14}$ | 6.3 |
| $n\text{-}C_{15}$ | 2.8 |
| $n\text{-}C_{16}$ | 0.6 |
| $n\text{-}C_{17}$ | <.1 |
| Total n-paraffins: | 42.7 |
| Vol. % | |
| Aromatics | 7.8 |
| Olefins | 0.0 |
| Paraffins + Naphthenes | 92.2 |
| | 100.0 |

The first desorbent material was mixed xylenes and the sweeping agent was isooctane. The first desorbent material was charged into zone 2 of the process in admixture (in several concentration levels) with the sweeping agent. The second desorbent material was normal pentane which was charged to zone 3 in admixture with isooctane. A 50/50 vol. % blend of normal pentane and isooctane was used. All experiments were conducted at approximately 350° F. and a pressure of approximately 300 psig.

In controlling the operating conditions for the various experiments, an important factor which was considered was the reflux ratio occurring within the various zones of operation. The reflux ratio within the given zone is defined as the net liquid flow into the zone in question minus the non-selective void volume of the adsorbent which passes into that zone, the above quantity all over the selective pore volume of adsorbent passing into the zone. The reflux ratio is presented in equation 2 below.

Equation 2:

$$\text{Reflux Ratio} = \frac{\text{Liquid Flow into Zone} - \text{Non-Selective Void Volume of Adsorbent Passing into Zone}}{\text{Selective Pore Volume of Adsorbent Passing into Zone}}$$

Therefore, it can be seen that in instances where the reflux ratio is 0 the liquid flow into a zone is exactly equal to the non-selective void volume of the adsorbent passing into that zone. In instances in which the reflux ratio is a positive number, the net liquid flow into the zone in question exceeds the volume of the non-selective voids of the adsorbent entering that zone which allows the liquid flowing into the zone to purge any liquid entrained by the adsorbent's non-selective void volume passing into that zone. In instances in which the overall reflux ratio is a negative number, the volume of liquid present in the non-selective void volume of the adsorbent which passes into the zone in question exceeds the liquid flow rate into that zone. This means the liquid trapped by the adsorbent in the non-selective voids is not totally removed from the adsorbent prior to its passing into the zone.

The reflux ratio of the zones in the experiments were positive so that there was enough liquid flowing into each zone from an input stream or from material bypassing an output stream from a zone immediately upstream from the zone in question, to effectively purge the adsorbent.

Four experiments were performed to show the reduced concentration of contaminant aromatics in the extract product made possible by my invention. The results of the four experiments along with the basic operating conditions necessary to reproduce them are shown in Table No. 2 below.

Table No. 2

| Experiment Results | | | | |
|---|---|---|---|---|
| Experiment | 1 | 2 | 3 | 4 |
| Flow Rates, gph at 60° F. | | | | |
|   Feed Stream | 1.67 | 1.62 | 1.66 | 1.74 |
|   First Desorbent + Sweep. Agent into Zone 2 | 1.52 | 1.52 | 1.54 | 1.54 |
|   Second Desorbent + Isooctane into Zone 3 | 8.16 | 8.29 | 8.10 | 8.23 |
| Reflux Ratios | | | | |
|   Zone 2 | 112.5 | 115.2 | 114.8 | 114.7 |
|   Zone 4 | 49.1 | 50.0 | 49.8 | 49.8 |
| % Xylene in First Desorbent + Sweep. Agent Mixture | 0 | 8 | 26 | 44 |
| Wt. % n-paraffins in Extract Product | 99+ | 99+ | 99+ | 99+ |
| Net Aromatics in Extract Product, wt. ppm | 1400 | 1200 | <100 | <100 |
| Efficiency of Extraction*, % | 96.0 | 94.5 | 93.5 | 91.5 |

* Defined as the ratio of extract material in the extract stream over the quantity of extract material in both the raffinate and extract streams.

For experiment 1 the first desorbent material (mixed xylenes) was not used; only sweeping agent (isooctane) entered zone 2. The concentration of aromatics in the extract product was 1400 wt. ppm. for experiment 1. For experiments 2, 3 and 4 the mixture of first desorbent material plus sweeping agent contained respectively 8, 26 and 44 vol. % mixed xylenes and produced concentrations of aromatics in the extract product of 1200, <100, and <100 wt. ppm. respectively, thus demonstrating the advantage of my process. Aromatics concentrations less than about 100 wt. ppm. could not be more precisely quantified because of lack of exact analytical techniques in the low ppm. range. Efficiency of extraction was affected by the use of a first desorbent material in zone 2 as shown by the decline from 96.0% efficiency with no first desorbent for experiment 1 to 91.5% obtained when 44% xylene was employed for experiment 4. This apparently is due to the selectivity of the 5A molecular sieve adsorbent for the xylenes. The xylenes are surface adsorbed leaving the interior sieve lattice partially blocked for normal paraffin adsorption resulting in a lowering of product recovery.

I claim as my invention:

1. In a process for the separation of normal paraffins from a feed stream containing a mixture of normal paraffins and isoparaffins along with aromatic hydrocarbons which process employs an adsorbent consisting essentially of a 5A zeolite and comprises the steps of:
   a. contacting said adsorbent with said feed at adsorption conditions to effect the selective adsorption of normal paraffins and a portion of the aromatic hydrocarbons by said adsorbent;
   b. removing a raffinate stream comprising less selectively adsorbed isoparaffins from said adsorbent;
   (c) contacting said adsorbent with a desorbent material at desorption conditions to effect the desorption of normal paraffins from said adsorbent;
   (d) removing from said adsorbent an extract stream comprising normal paraffins, and;
   (e) passing at least a portion of said extract stream to a separation means and therein separating at separation conditions normal paraffins from desorbent material, The improvement which comprises using a two-step desorption operation which comprises the steps of:
   i. contacting at first desorption conditions said adsorbent with a first desorbent material, said material comprising an aromatic hydrocarbon having a boiling point different than said mixture to effect the desorption of said feed aromatic hydrocarbons;
   ii. removing a first extract stream comprising said feed aromatic hydrocarbons and said first desorbent material from said adsorbent;
   iii. contacting at second desorption conditions said adsorbent with a second desorbent material to effect the desorption of normal paraffins:
   iv. removing a second extract stream comprising normal paraffins and second desorbent material from said adsorbent; and
   v. passing at least a portion of said second extract stream to a separation means and therein separating at separation conditions normal paraffins from said second desorbent material.

2. The process of claim 1 further characterized in that said feed stream has a carbon number range of from about 6 to about 30 carbon atoms per molecule.

3. The process of claim 1 further characterized in that said second desorbent material comprises normal paraffins having a different boiling point than that of the normal paraffins in the feed stream.

4. The process of claim 1 further characterized in that said adsorption conditions, first desorption conditions and second desorption conditions, include a temperature within the range of from about 40° C. to about 250° C. and a pressure of from about atmospheric to about 500 psig.

5. In a process for the separation of normal paraffins from a feed stream comprising a mixture of normal paraffins, isoparaffins and aromatic hydrocarbons which process employs an adsorbent consisting essentially of a 5A zeolite and comprises the steps of:
   a. maintaining net fluid flow through a column of said adsorbent in a single direction, which column contains at least three zones having separate operational functions occurring therein and being serially interconnected with the terminal zones of said column connected to provide a continuous connection of said zones;
   b. maintaining an adsorption zone in said column, said zone defined by the adsorbent located between a feed input stream at an upstream boundary of said zone and a raffinate output stream at a downstream boundary of said zone;
   c. maintaining a purification zone immediately upstream from said adsorption zone, said purification zone defined by the adsorbent located between an extract output stream at an upstream boundary of said purification zone and said feed input stream at a downstream boundary of said purification zone, said purification zone having a sweeping agent input stream located upstream from said feed input stream;
   d. maintaining a desorption zone immediately upstream from said purification zone, said desorption zone defined by the adsorbent located between a desorbent input stream at an upstream boundary of said zone and said extract output stream at a downstream boundary of said zone;
   e. passing said feed stream into said adsorption zone at adsorption conditions to effect the selective adsorption of normal paraffins and aromatics by said adsorbent in said zone and withdrawing a raffinate output stream comprising isoparaffins from said zone;
   f. passing a desorbent input stream into said desorption zone at desorption conditions to effect the displacement of normal paraffins from the adsorbent in said zone and withdrawing an extract output stream comprising normal paraffins and desorbent material from said zone;
   g. passing at least a portion of said extract output stream to a separation means and therein separating at separation conditions normal paraffins from desorbent material;
   h. passing a sweeping agent having a boiling point different than said mixture into said purification zone;
   i. periodically advancing through said column of adsorbent in a downstream direction with respect to fluid flow in said adsorption zone the feed input stream, raffinate output stream, desorbent input stream, and extract output stream to effect the shifting of zones through said adsorbent and the production of extract output and raffinate output streams, wherein the improvement comprises using a two-step desorption operation which comprises the steps of:
   i. passing into said purification zone in admixture with said sweeping agent a first desorbent material, said material comprising an aromatic hydrocarbon having a boiling point different than said mixture and therein desorbing at first desorption conditions aromatics from said adsorbent;
   ii. withdrawing a raffinate output stream comprising feed isoparaffins and aromatic hydrocarbons, sweeping agent and first desorbent material from said adsorption zone;

iii. passing into said desorption zone a second desorbent material and therein desorbing at second desorption conditions normal paraffins from the adsorbent;

iv. removing an extract output stream comprising normal paraffins and said second desorbent material from said desorption zone; and, v. passing at least a portion of said extract output stream to a separation means and therein separating at separation conditions normal paraffins from said second desorbent material to produce a normal paraffin product containing a low concentration of aromatic hydrocarbons.

6. The process of claim 5 further characterized in that said feed stream has a carbon number range of from about 6 to about 30 carbon atoms per molecule.

7. The process of claim 5 further characterized in that it includes the step of maintaining a buffer zone immediately upstream from said desorption zone, said buffer zone defined as the adsorbent located between the desorbent input stream at a downstream boundary of said buffer zone and a raffinate output stream at an upstream boundary of said buffer zone.

8. The process of claim 5 further characterized in that said first desorbent aromatic hydrocarbon is selected from the group consisting of benzene, toluene, ethylbenzene and the xylene isomers.

9. The process of claim 5 further characterized in that said first desorbent material comprises from about 5 vol. % to about 100 vol. % of the mixture of sweeping agent and first desorbent material.

10. The process of claim 5 further characterized in that said mixture of sweeping agent and first desorbent material contains less than about 1 vol. % of said second desorbent material.

11. The process of claim 5 further characterized in that said second desorbent material comprises a normal paraffin having a boiling point different than that of the feed material to permit separation therefrom by distillation.

12. The process of claim 11 further characterized in that said second desorbent material comprises normal pentane.

13. The process of claim 5 further characterized in that said second desorbent material contains less than about 0.1 vol. % of said first desorbent material.

14. The process of claim 5 further characterized in that said concentration of aromatic hydrocarbons in said normal paraffin product is less than about 100 wt. ppm.

* * * * *